(12) United States Patent
Clark

(10) Patent No.: US 10,660,747 B2
(45) Date of Patent: May 26, 2020

(54) MEMORY MATERIAL VALVE

(71) Applicant: Alan Clark, Raleigh, NC (US)

(72) Inventor: Alan Clark, Raleigh, NC (US)

(*) Notice: Subject to any disclaimer, the term of this patent is extended or adjusted under 35 U.S.C. 154(b) by 150 days.

(21) Appl. No.: 15/793,714

(22) Filed: Oct. 25, 2017

(65) Prior Publication Data

US 2019/0117389 A1    Apr. 25, 2019

(51) Int. Cl.
*A61F 2/24* (2006.01)
*F16K 27/02* (2006.01)
*A61F 2/90* (2013.01)
*A61F 2/88* (2006.01)

(52) U.S. Cl.
CPC .......... *A61F 2/2415* (2013.01); *A61F 2/2412* (2013.01); *A61F 2/2418* (2013.01); *A61F 2/2427* (2013.01); *F16K 27/0209* (2013.01); *A61F 2/88* (2013.01); *A61F 2/90* (2013.01); *A61F 2210/0023* (2013.01); *A61F 2230/0091* (2013.01); *A61F 2240/001* (2013.01)

(58) Field of Classification Search
CPC .... A61F 2/2415; A61F 2/2412; A61F 2/2418; A61F 2/2427; A61F 2/88; A61F 2/90; A61F 2210/0023; A61F 2230/0091; A61F 2240/001; F16K 27/0209
USPC .......................................... 29/428
See application file for complete search history.

(56) References Cited

U.S. PATENT DOCUMENTS

| | | | | |
|---|---|---|---|---|
| 4,245,358 A * | 1/1981 | Moasser | ............... | A61F 2/2403 137/533.11 |
| 5,855,602 A * | 1/1999 | Angell | ................... | A61F 2/2409 606/1 |
| 6,102,944 A * | 8/2000 | Huynh | .................. | A61F 2/2409 623/2.14 |
| 6,440,164 B1 * | 8/2002 | DiMatteo | ............... | A61F 2/2412 623/1.24 |
| 7,153,324 B2 * | 12/2006 | Case | ...................... | A61F 2/2412 623/1.24 |
| 7,682,390 B2 * | 3/2010 | Seguin | .................. | A61B 17/072 623/1.26 |
| 2001/0044629 A1 * | 11/2001 | Stinson | ............ | A61B 17/12022 606/108 |
| 2003/0055496 A1 * | 3/2003 | Cai | ........................ | A61F 2/2412 623/2.19 |
| 2005/0222557 A1 * | 10/2005 | Baxter | ............... | A61B 18/1492 606/16 |

* cited by examiner

*Primary Examiner* — Justin M Jonaitis
(74) *Attorney, Agent, or Firm* — Daniel Becker; Olive Law Group, PLLC

(57) ABSTRACT

A replacement heart valve comprising a memory shape element. The various embodiments use internal body heat to seat and retain the valve within a blood passage. The element can be provided in a variety of shapes and sizes, and is at least partially encased within an inert and pliant encasing material. The encasing material is one that is adapted to be contiguous with the structure of the valve nozzle or back-flow-resistant leaf structure, and may be used in combination with existing stents or an incorporated stent, including ones having a structure similar to conventional stents.

12 Claims, 5 Drawing Sheets

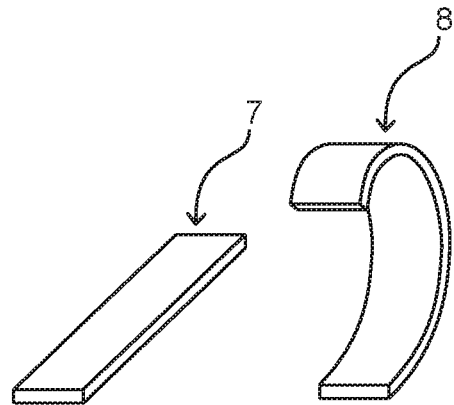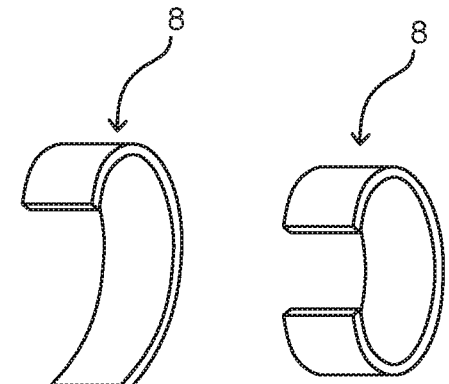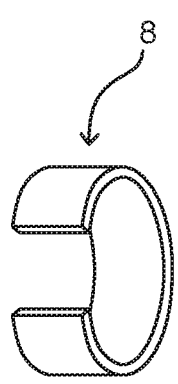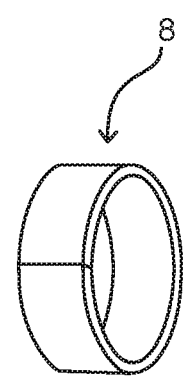
FIG.3(a)   FIG.3(b)   FIG.3(c)   FIG.3(d)
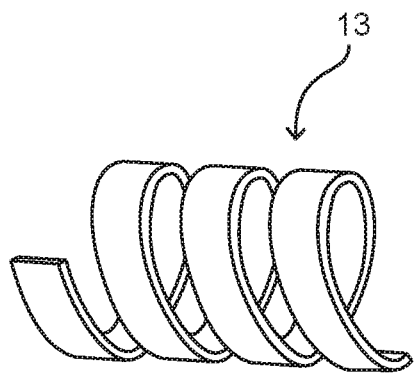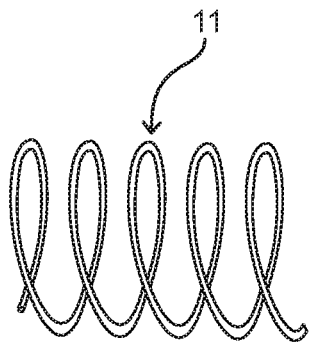
FIG.4   FIG.5

MEMORY MATERIAL VALVE

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

FIELD

At least some embodiments disclosed herein relate, in general, to valves and more specifically to replacement heart valves.

BACKGROUND

Heart valve repair and replacement is a procedure that has been practiced on many animals, including human beings. They were both end of life and disease-warranted circumstances that lead up to a decision to perform repairs to the heart. Many of these procedures require opening the chest cavity and cutting into the heart, in order to access the natural valves and sew-in a replacement valve structure. There are artificial valves and biological valves, and hybrids of the two.

For the most part, these require the open chest procedures. Open-heart surgeries have long recovery times and expose the patient to infection, as well as a higher chance of death as a result of the procedure or during the procedure, during which the heart is stopped and an artificial pumping system is used to maintain blood flow throughout the patient's body.

A relatively late development is that of repairing heart valves intravenously. There are some very recent developments in providing a replacement valve to the site of a natural valve via an intravenous catheter. However, these valves are expensive and must be a specific fit, so available valves are not always optimal. A high degree of skill is therefore necessary in installing the valve into any particular patient, because it may not be exactly the right size. Also, because the size of the replacement valves sit during surgery, over time, with growth and other health changes, it may become in correctly sized to maintain a secure fit.

What is missing in the art is a valve that can deliver a replacement valve to the site of a damaged or incorrectly functioning natural valve, be installed by intravenous catheter, and which can adapt to fit a wide variety of patients and valves, and which maintains a secure fit at the site over an extended period of time.

Also, patients and/or doctors must make a decision between using biological material valves and mechanical valves. Mechanical valves last many years longer than biological valves (which are typically made from the valves of swine or cows), but they are noisy, and are not well-suited for younger patients, because they are rigid and less pliant to match the changing shape and size of the heart than biological valves, and therefore require several more surgeries over the course of the child's growth into adulthood.

SUMMARY

The present invention provides several embodiments of valves that can be delivered to the site of a damaged or incorrectly functioning natural valve, and installed by intravenous catheter. It can adapt to fit a wide variety of patients and any of the valves of their hearts. It also exploits provides a special construction to maintain a secure fit at the site over an extended period of time, comparable to biological valves, but with the silent operation of valves made from biological materials.

Various embodiments of the present invention achieve these advantages by replacing the typical expanding scaffold stent (to which most existing valves are attached), with a memory shape element. The element can be shaped in the form of several alternative geometries, such as a rolled ply of memory shaped metal, or helically-rolled ribbon of memory shape metal, or a coil of memory shape wire. These are merely exemplary. The invention also contemplates variations of existing stenting structures, such as an expanding stand also made of memory shape materials. An example of an excellent memory shape material for these applications is Nickel-Titanium alloy.

In practice, the memory shape element of the valve would be sized or otherwise bent or manipulated into a desired shape to fit an intended valve to repair for the patient, and then heated to a sufficiently high temperature that the memory shape element becomes "set" to this memory shape. After setting the valve's memory shape element to the desired memory shape, the valve would be drawn or tightened or otherwise collapsed to a small enough diameter such that it is fit tightly to an intravenous catheter. Once fit onto a catheter, the valve is ready to be delivered to the site of a patient's natural valve in an intravenous surgical procedure.

To minimize the risk of a patient experiencing an adverse reaction to the memory shape material, the memory shape element is at least partially encased in an inert encasing material, such as silicone. Silicone has advantages of being very flexible, soft, malleable, and having a high temperature tolerance.

Further, when heated, silicone can be formed into several geometries that could function as a valve, in many instances, the encasing material being fully contiguous with the structure of the valve. For example, a "plug" of silicone, including any number of circumferential shapes of memory shape material, could be drawn tightly into the shape of a flattened nozzle, and then cut, to form a single-piece 1-way check valve. In such an embodiment, the valve would be dramatically more silent than existing valves, which snap shut as chambers of the heart relax.

The material is also versatile enough that it could support any number of existing geometries, such as two-leaf and three-leaf valves that replicate the shape and function of natural bicuspid and tricuspid valves, for example.

In installation, the valve and memory shape element, after being delivered to the site of the natural valve to be repaired, can be expanded to a size which fits securely. The ambient temperature of the body causes the valve to expand toward its pre-set memory-shape, and therefore the valve naturally adopts a fit that securely engages the entire breadth of the passage. Fitting the memory shape element towards its memory shape position or otherwise expanding it may be assisted by many existing methods, such as a balloon expansion or any other method similar to installing an expandable stent.

Another difference between such an embodiment of a present invention and existing valve-seating scaffolding and devices is that the memory shape element can use the ambient temperature of the chest of the patient to maintain the valve securely, even as the patient grows, ever pushing toward its memory shape position, preferably set to be just-larger than the anticipated maximum size of site the patient's natural valve.

Also, if the valve should need to be resized it can be adjusted again, or even removed, by a catheter, without needing to disassemble any part of the valve. It remains a single piece during its entire period of use.

In some contemplated alternative embodiments, other mechanical and biological valves may be connected to an encased memory shape element of the present invention, essentially providing the invention as a versatile semi-universal "memory shape stent" or "memory shape scaffold," which affords existing valves of the prior art with the advantages of a memory-shape-seated fit that is maintained over time by temperature-driven expansion of the valve.

In several other embodiments, the valve may be supplemented with memory shape materials that extend beyond the encasing material, if the risk of reaction is low. This is especially desirable in the cases of a helical coil or ribbon memory shape element. To tighten the fit of these helical six sections against the wall of a blood-passage, a counter-wound coil may also be included, and arranged coaxially to the first coil. This way, as the two coils expand, they press against one another to create intersection points which provide friction against spiraling the valve lengthwise, providing additional resistance against drift of the valve with respect to the site of the natural valve, over time.

Other secondary elements may be used in order to locate the valve, either by these components extending out or away from the structure or the valve, or by mimicking or merely using other devices of the prior art, such as expanding stents, to provide a secure mounting location for a version of the valve.

Additionally, embodiments of the valve are contemplated which provide a second encased memory shape material element at a free end of such a supplemental stenting structure. In such embodiments, the second encased memory shape element would essentially provide a second circumferential region at which the valve would engage the blood passage, fortifying the fit of the valve to the passage. A secondary memory shape element could be located upstream or downstream of the first memory shape element.

BRIEF DESCRIPTION OF THE DRAWINGS

The embodiments are illustrated by way of example and not limitation in the figures of the accompanying drawings in which like references indicate similar elements.

FIG. 3(a) shows a perspective view of a ply of a memory shape material in accordance with the present disclosure.

FIG. 3(b) shows a perspective view of a ply of a memory shape material as partially rolled into a memory shape element of a valve in accordance with the present disclosure.

FIG. 3(c) shows a perspective view of a ply of a memory shape material as partially rolled into a memory shape element of a valve in accordance with the present disclosure.

FIG. 3(d) shows a perspective view of a ply of a memory shape material fully rolled into a memory shape element of a valve in accordance with the present disclosure.

FIG. 4 shows a perspective view of a helical ribbon memory shape element for a valve in accordance with the present disclosure.

FIG. 5 shows a perspective view of a helical coil memory shape element for a valve in accordance with the present disclosure.

DETAILED DESCRIPTION

The following description and drawings are illustrative and are not to be construed as limiting. Numerous specific details are described to provide a thorough understanding. However, in certain instances, well known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Referring to FIGS. 1, 2, and 6-10, each has a valve (5) comprising an inert encasing material (3), and at least one memory shape element at least partially encased within the encasing material (3).

Figure 1:
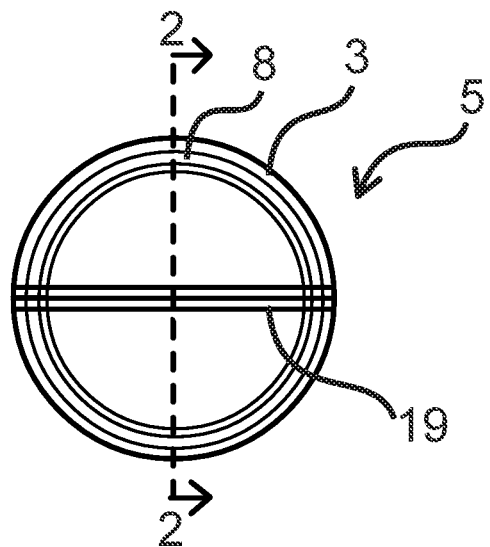
FIG. 1 Shows a front view of an embodiment of a valve in accordance with the present disclosure.
Figure 2:
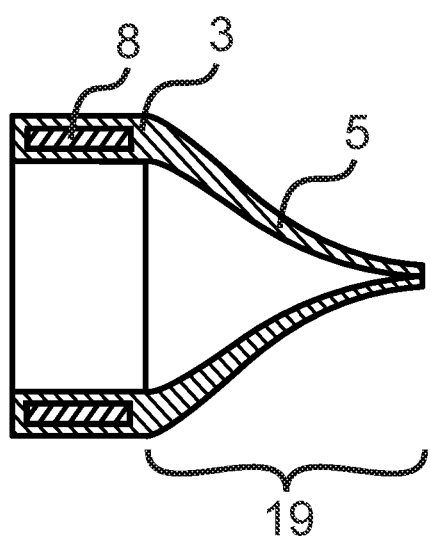
FIG. 2 shows a section view of an embodiment of a valve in accordance with the present disclosure.

Referring now to FIGS. 1 and 2, the encasing material (3) comprises a distending nozzle (19) and the memory shape element is a circumferential ring memory shape element (8).

Referring now to FIGS. 3a, 3b, and 3c, a memory shape material metal ply (7) is shown as flat in FIG. 3a, and as a partially rolled into a circumferential ring (8), shown partially rolled in FIGS. 3b and 3c, and fully rolled in FIG. 3c.

Referring now to FIG. 4 and FIG. 5, what are shown are alternative shape memory shape elements. FIG. 4, a ribbon of memory shape material is wrapped into a helical ribbon (13), and in FIG. 5, a wire of memory shape material is wrapped into a helical coil (11).

Figure 6:
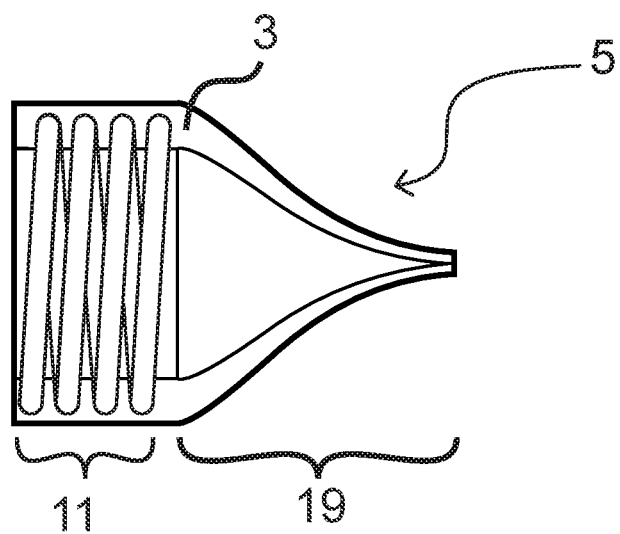
FIG. 6 shows an elevation view of an embodiment of a valve with a helical coil memory shape element in a translucent encasement material in accordance with the present disclosure.

In FIG. 6, what is shown as an elevation view of a valve (5). Like FIG. 2, this valve (5) has an encasing material (3), a distending nozzle (19), but wherein the memory shape element is a memory shape wire wrapped into a helical coil (11). The memory shape helical coil (11) in this embodiment is visible because the encasing material (3) is translucent.

Figure 7:
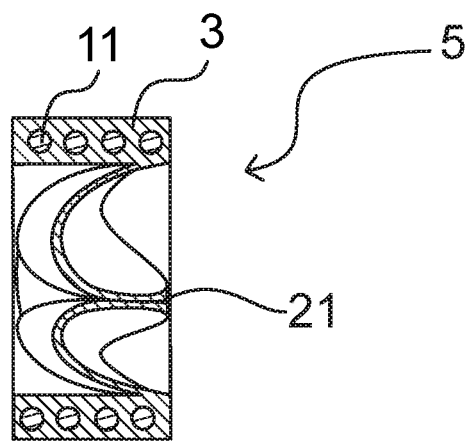
FIG. 7 shows a section view of an embodiment of a valve with a helical with a three-leaf construction in accordance with the present disclosure.

In FIG. 7, there is shown a sectioned elevation view of a valve (5) that, like FIG. 2, has a encasing material (3), a memory shape element (1), but where in the valve (5) is a three leaf valve (21) construction, rather than a nozzle (19, FIG. 2).

Figure 8:
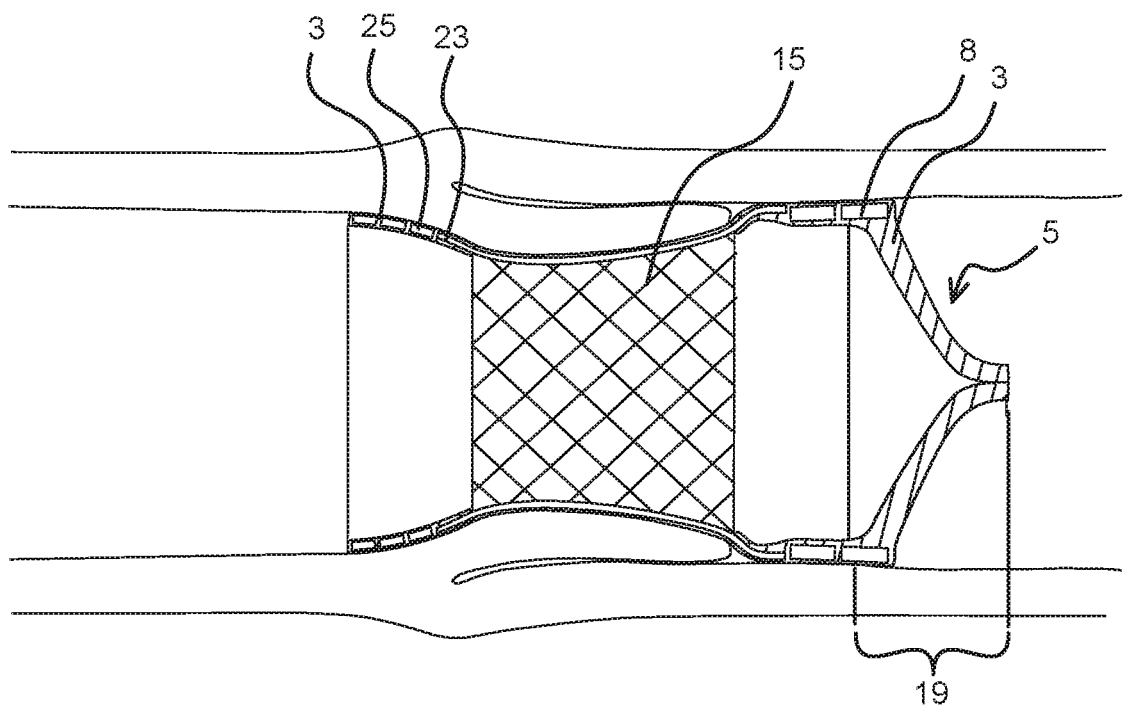
FIG. 8 shows a section view of an embodiment of a valve as installed in a blood-passage in accordance with the present disclosure.
Figure 9:
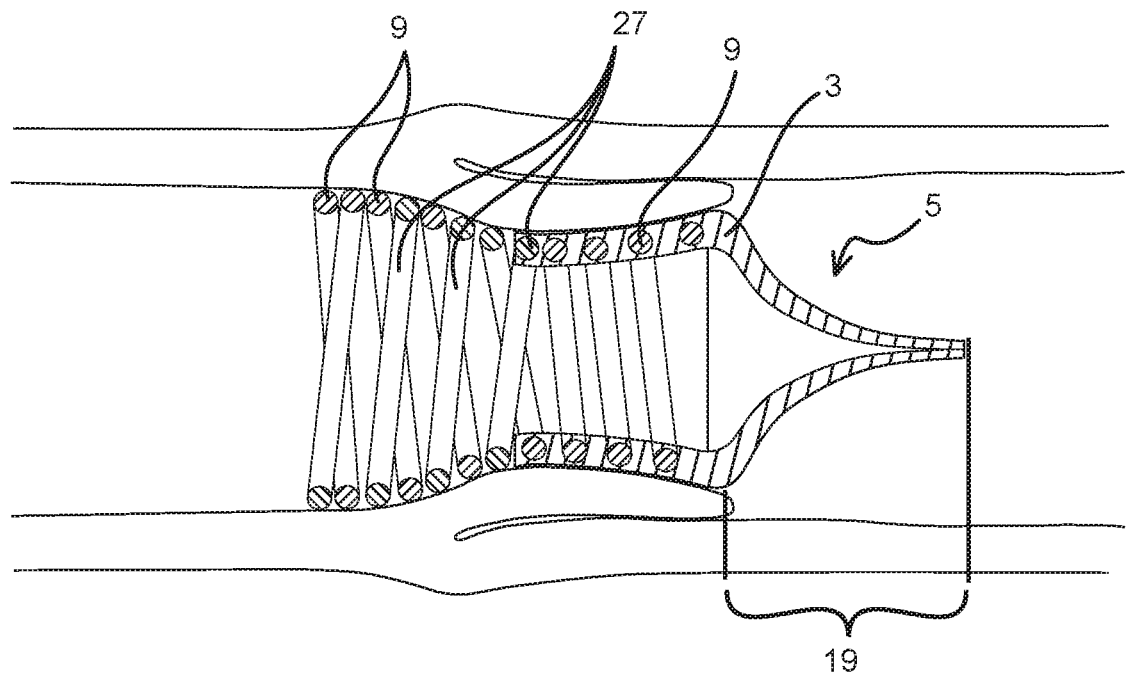
FIG. 9 shows a section view of an embodiment of a valve having a counter-rotation coil in accordance with the present disclosure.

In FIGS. 8 and 9, there are shown sectioned elevation views of alternative valve embodiments as installed into a blood passage of a mammal, each the result of a valve-repair or valve-replacement procedure.

In FIG. 8, the valve (5) is similar to that of FIG. 2, comprising an encasing material (3), a memory shape element ring (8), and a nozzle (19). Here, though, the valve (5) is augmented with a supplemental stent (15), a similar construction to that of a conventional expandable stent, but this supplemental stent is partially encased in the encasing material (3). At a free end (23) of the supplemental stent (15) is a second memory shape element (25), also encased in encasing material (3).

In FIG. 9, a valve (5) similar to FIG. 6, instead comprising a partially encased helical coil memory shape element (9) that extends away from the nozzle (19), beyond the encasing material (3), and a counter-wound helical coil (27). The counter-wound helical coil (27) is coaxial with the partially encased helical coil (9), so that when the valve (5) is returned to the pre-set memory shape, the counter-wound helical coil (27) comes into contact with the helical coil (9) and creates friction against slippage, to ensure that the valve (5) fits securely when installed, and to its desired, pre-set shape.

Figure 10:
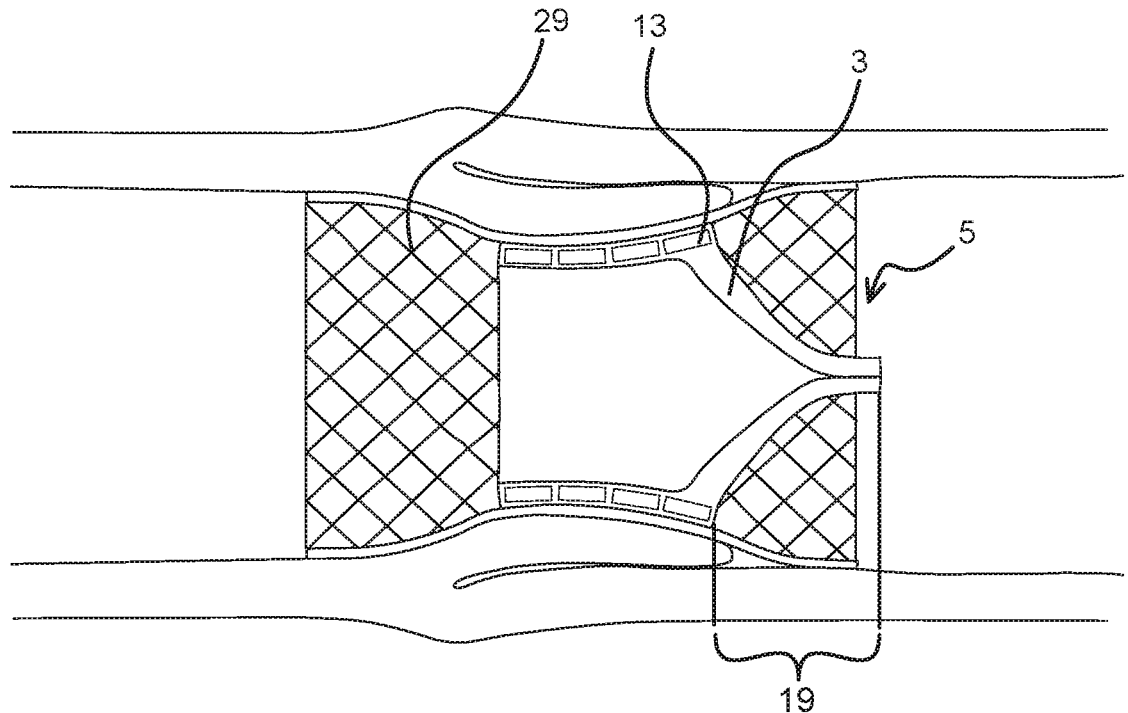
FIG. 10 shows a section view of an embodiment of a valve as installed in a blood-passage with a conventional stent in accordance with the present disclosure.

In FIG. 10, the encasing material (3) of the valve (5) has a nozzle (19) and encases a helical ribbon memory shape element (13), but its valve (5) is fit-into a conventional-style stent (29), rather than the valve (5) being incorporated with a supplemental stent (FIG. 8, (15)).

Figure 11:
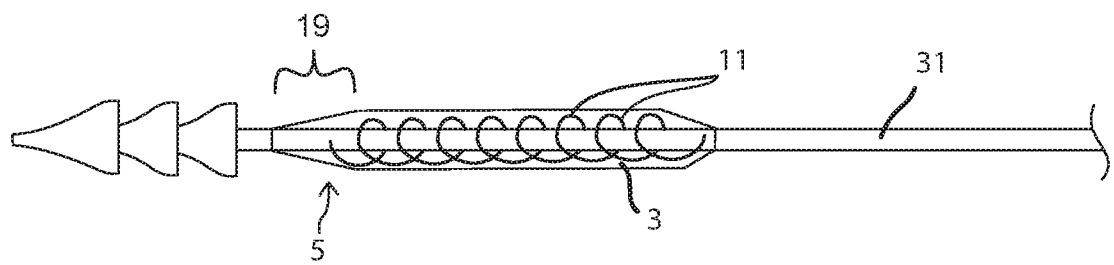
FIG. 11 shows a valve of the present invention as collapsed to fit onto a catheter.

FIG. 11 shows an embodiment of the present invention that is similar to FIG. 6, but is shown with a nozzle (19), coil (11), and encasing material (3), all collapsed onto a catheter (31). In this arrangement, the valve (5) may be delivered to a location in a blood passage intravenously.

In the foregoing specification, the disclosure has been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

I claim:

1. A valve for modulating bloodflow in a blood passage, comprising:
    a body defining a proximal end and a distal end wherein the proximal end defines a memory shape element configured for applying longitudinal and hoop pressure to the proximal end at a site for modulating bloodflow, wherein the distal end defines a memory shape element configured to extend along the length of the passage to fit the variation in diameter and curvature along the length of the passage extending away from the site.

2. The valve of claim 1, wherein a stent component is positioned between the proximal end and the distal end.

3. The valve of claim 1, wherein the memory shape element of the proximal end comprises a shape selected from a list comprising a helical coil and a helical ribbon and the memory shape element of the distal end comprises a shape selected from a list comprising a helical coil and a helical ribbon, wherein the memory shape element of the distal end is counter-wound, such that the memory shape element of the distal end is configured to create intersection points with respect to the memory shape element of the proximal end, which provide friction against spiraling the valve lengthwise along the length of a blood passage.

4. The valve of claim 1, wherein the proximal end comprises an encasing material and the distal end comprises an encasing material that is independent and non-contiguous with the encasing material of the proximal end.

5. The valve of claim 1, wherein the proximal end comprises an encasing material and a valve structure integrally formed with the encasing material.

6. A valve for modulating bloodflow in a blood passage comprising:
    a 1st memory shape element at least partially encased in a first encasing material,
    a valve structure integrally formed within the first encasing material,
    a second memory shape element at least partially encased in a second encasing material,
    a supplemental element disposed between the first and second memory shape elements,
    wherein the first memory shape element is configured to be spaced apart from the second memory shape element by the supplemental element,
    wherein the first memory shape element is configured to apply longitudinal and hoop pressure to a passage at a site where fluid flow is modulated;
    wherein the second memory shape element is configured to apply longitudinal and hoop pressure along the length of the passage away from the fluid flow modulation site.

7. The valve of claim 6, wherein the supplemental element is a stent.

8. The valve of claim 6, wherein the supplemental element comprises a memory shape material and is configured to define the offset distance of the second memory shape element from the first memory shape element along the length of the passage when heat is applied to the memory shape element.

9. The valve of claim 6, wherein the second memory shape element comprises a shape configured to extend lengthwise upon restriction of diameter increase, selected from a list comprising a helical coil and a helical ribbon.

10. The valve of claim 6, further comprising a third memory shape element at least partially encased in the first encasing material, arranged on the side of the supplemental element opposite of the first memory shape element.

11. A valve for modulating bloodflow in a blood passage, comprising:
    a first memory shape element at least partially encased in an encasing material,
    a valve structure that is integrally formed with the first encasing material,
    a supplemental element,
    a second memory shape element at least partially encased in a second encasing material that is noncontiguous with the first encasing material,
    wherein the first memory shape element comprises a ring of memory shape material,
    wherein the supplemental element is a stent and comprises a memory shape material,
    wherein the second memory shape element comprises a helical ribbon of memory shape material,
    wherein the material of the second encasing material is interspersed between the coils of the helical ribbon.

12. A valve for modulating bloodflow in a blood passage, comprising:

a first memory shape element a least partially encased in an encasing material, a valve structure that is integrally formed with the first encasing material, wherein a portion of the first memory shape element extends out of the encasing material, away from the valve, along the length of a passage, a second memory shape element, at least partially encased in the encasing material that extends out of the encasing material, away from the valve, along the length of the passage, wherein the first memory shape element is a helical coil, wherein the second memory shape element is a counter wound helical coil, configured to resist spiraling and drifting.

* * * * *